United States Patent
Baba

(10) Patent No.: US 7,468,510 B2
(45) Date of Patent: Dec. 23, 2008

(54) SPEEDUP IN COORDINATE DIFFERENCE CALCULATION

(75) Inventor: Kiyoshi Baba, Minato-ku (JP)

(73) Assignee: NEC Corporation, Tokyo (JP)

( * ) Notice: Subject to any disclaimer, the term of this patent is extended or adjusted under 35 U.S.C. 154(b) by 255 days.

(21) Appl. No.: 11/585,166

(22) Filed: Oct. 24, 2006

(65) Prior Publication Data

US 2007/0114378 A1     May 24, 2007

(30) Foreign Application Priority Data

Oct. 25, 2005     (JP)     ............................. 2005-309827

(51) Int. Cl.
*G01F 19/00*     (2006.01)
*B01D 59/44*     (2006.01)
(52) U.S. Cl. .................. 250/251; 250/284; 702/41; 702/49
(58) Field of Classification Search ............... 250/251, 250/284; 702/41, 49
See application file for complete search history.

(56) References Cited

U.S. PATENT DOCUMENTS

2007/0118302 A1*   5/2007   Watanabe ............... 702/41

FOREIGN PATENT DOCUMENTS

| JP | 06-176052 A | 6/1994 |
|----|-------------|--------|
| JP | 06-223052 A | 8/1994 |
| JP | 06-231114 A | 8/1994 |

* cited by examiner

*Primary Examiner*—Nikita Wells
(74) *Attorney, Agent, or Firm*—Sughrue Mion, PLLC

(57) ABSTRACT

A coordinate difference calculation apparatus of the present invention is a coordinate difference calculation apparatus for calculating a coordinate difference between an i-particle and a j-particle included in one of a plurality of minute cells obtained by dividing a basic cell, includes a first storage section that stores in advance a coordinate value of the i-particle, a second storage section that stores in advance a value obtained by adding the length of one side of the basic cell to the coordinate of the i-particle, a third storage section that stores a value obtained by subtracting the length of one side of the basic cell from the coordinate of the i-particle, a control section that outputs a selection signal to select a value in order to minimize the distance between a minute cell including the i-particle and a minute cell including the j-particle among the values stored in the first to third storage sections and that outputs a coordinate value of the j-particle, a selection section that selects any one of the values stored in the first to third storage sections and outputs a selected value, and a computing section that subtracts the value output from the selection section from the coordinate of the j-particle output from the control section.

4 Claims, 6 Drawing Sheets

US 7,468,510 B2

SPEEDUP IN COORDINATE DIFFERENCE CALCULATION

This application is based upon and claims the benefit of priority from Japanese Patent Application No. 2005-309827 filed on Oct. 25, 2005, the content of which is incorporated by reference.

BACKGROUND OF THE INVENTION

1. Field of the Invention

The present invention relates to a coordinate difference calculation apparatus and a coordinate difference calculation method for calculating a difference between coordinates of two particles.

2. Description of the Related Art

In molecular dynamics, when the force acting on i-particle is calculated, all particles except i-particle are regarded as j-particles, and the total of forces acting between i-particle and each j-particle is obtained. Generally, since the force acting between two particles depends on the distance between the particles, first, there is a need to obtain the distance between the particles.

However, when all particles except i-particle are regarded as j-particles, the calculation amount is enormous. So, in recent years, the force acting on i-particle is calculated according to the periodic boundary condition.

In the periodic boundary condition, a predetermined basic cell in a rectangular parallelepiped shape is considered, and only particles existing in the same basic cell as the i-particle are regarded as j-particles. Also, it is assumed that j-particles are arranged in each of the surrounding basic cell in the same way, a j-particle that provides the minimum distance from an i-particle is regarded as an object to be calculated among j-particles existing in the same basic call as the i-particle and in the surrounding basic cells, and the force acting on an i-particle from a j-particle, which is the object to be calculated, is calculated.

Hereinafter, detailed explanations are given of the periodic boundary condition with reference to FIG. 1 to FIG. 3.

FIGS. 1 to 3 are two-dimensional views showing basic cells in the XY-plane. Incidentally, in FIG. 1 to FIG. 3, each basic cell has a side that is Lx in length in the X-axis direction, a side that is Ly in length in the Y-axis direction, and a side that is Lz in length in the Z-axis direction, not shown. Further, each basic cell is divided into a plurality of minute cells. Also, though there is generally a plurality of particles in each minute cell, in FIG. 1 to FIG. 3, only necessary particles are shown to simplify explanations.

In the example in FIG. 1, i-particle exists in the center basic cell. Also, j-particle exists in the same basic cell as i-particle, and it is assumed that j-particle exists also in each of the surrounding basic cell in the same way. Incidentally, hereinafter, for convenience of explanation, a j-particle in the same basic cell as an i-particle is called a $j_0$-particle and j-particles in surrounding basic cells are each called $j_1$- to $j_8$-particles. Among these $j_0$- to $j_8$-particles, a $j_0$-particle in the same basic cell as an i-particle provides the minimum distance from the i-particle. In this case, according to the periodic boundary condition, $j_0$-particle is regarded as the object to be calculated and the force acting on i-particle from $j_0$-particle is calculated.

On the other hand, in the example in FIG. 2, among $j_0$- to $j_8$-particles, the minimum distance from the i-particle is provided by the $j_6$-particle in the surrounding basic cell, not by the $j_0$-particle in the same basic cell as i-particle. In this case, according to the periodic boundary condition, the $j_6$-particle is regarded as the object to be calculated and the force acting on an i-particle from the $j_6$-particle is calculated.

Similarly, in the example in FIG. 3, among $j_0$- to $j_8$-particles, the minimum distance from the i-particle is provided by the $j_8$-particle in the surrounding basic cell, not by the $j_0$-particle in the same basic cell as i-particle. In this case, according to the periodic boundary condition, a $j_8$-particle is regarded as the object to be calculated and the force acting on an i-particle from the $j_8$-particle is calculated.

The method disclosed in Patent Document 1 (Japanese Patent Laid-Open No. 06-176052) is known as the method of obtaining the distance between particles according to the periodic boundary condition, as described above.

In the method disclosed in Patent Document 1, first, the coordinate difference between an i-particle and a $j_0$-particle in the same basic cell is calculated. Successively, the calculation result of the difference is compared with ±½ of the length of one side of the basic cell. Then, when the calculation result of the difference is larger than ½ of the length of one side of the basic cell, the length of one side of the basic cell is subtracted from the calculation result of the difference, and when the calculation result of the difference is smaller than −½ of the length of one side in the basic cell, the length of one side of the basic cell is added to the calculation result of the difference. According to this operation, the distance between particles is calculated based on the periodic boundary condition.

Specifically, when the coordinate difference in the X-axis direction is calculated in the example in FIG. 1, first, the coordinate difference between the i-particle and the $j_0$-particle is calculated. This case does not satisfy the requirement that the calculation result of the difference be larger than Lx/2 nor that the calculation result of the difference be smaller than −Lx/2. Therefore, neither addition nor subtraction of Lx is performed.

On the other hand, when the coordinate difference in the X-axis direction is calculated in the example in FIG. 2, first, the difference between an i-particle and a $j_0$-particle is calculated. In this case, it is assumed that the calculation result of the difference is larger than Lx/2. Therefore, Lx is subtracted from the calculation result of the difference, thereby calculating the coordinate difference between an i-particle and a $j_6$-particle.

Also, when the coordinate difference in the X-axis direction is calculated in the example in FIG. 3, first, the difference between an i-particle and a $j_0$-particle is calculated. In this case, it is assumed that the calculation result of the difference is smaller than −Lx/2. Therefore, Lx is added to the calculation result of the difference, thereby calculating the coordinate difference between an i-particle and a $j_8$-particle.

However, in the method disclosed in Patent Document 1, whenever an i-particle is changed, the calculation result of the coordinate difference is compared with ±Lx/2, and Lx is added or subtracted in accordance with the comparison result. Therefore, there is a need to dynamically calculate the periodic boundary condition. Accordingly, the calculation amount of the coordinate difference is increased, and speedup in calculation cannot be attained. Also, in order to enhance the speed of the calculation, a dedicated computing unit that dynamically calculates the periodic boundary condition is required, and the gate amount is increased.

SUMMARY OF THE INVENTION

Accordingly, it is an object of the present invention to provide a coordinate difference calculation apparatus and a coordinate difference calculation method that can try to speedup the coordinate difference calculation without using a dedicated computing unit.

To attain the above object, the present invention is applied to a coordinate difference calculation apparatus for calculating a coordinate difference between an i-particle and a j-particle included in one of a plurality of minute cells obtained by dividing a basic cell.

A coordinate difference calculation apparatus according to the present invention includes:

a first storage section that stored in advance a coordinate value of said i-particle;

a second storage section that stored in advance a value obtained by adding the length of one side of said basic cell to the coordinate of said i-particle;

a third storage section that stored in advance a value obtained by subtracting the length of one side of said basic cell from the coordinate of said i-particle;

a control section that outputs a selection signal to select a value to minimize the distance between a minute cell including said i-particle and a minute cell including said j-particle among the values stored in said first to third storage sections and that outputs a coordinate value of said j-particle;

a selection section that selects any one of the values stored in said first to third storage sections in accordance with the selection signal that is output from the control section and which outputs a selected value; and a computing section that subtracts the value that is output from said selection section, from the coordinate value of said j-particle that is output from said control section.

As described above, according to the present invention, as the periodic boundary condition that is constant during the time when the force acting on an i-particle is calculated, the coordinate value of an i-particle, the value obtained by adding the length of one side of the basic cell to the coordinate of i-particle, and the value obtained by subtracting the length of one side of the basic cell from the coordinate of the i-particle are stored in advance. When the coordinate of the difference between an i-particle and a j-particle is calculated, first, the periodic boundary condition is selected so as to minimize the distance between the minute cell including the i-particle and the minute cell including the j-particle. Then, the selected periodic boundary condition is subtracted from the coordinate of the j-particle, whereby the coordinate difference is calculated.

Therefore, since there is no need to dynamically calculate the periodic boundary condition whenever a j-particle is changed, the present invention allows calculating the coordinate difference at high speed without using a dedicated computing unit, which is different from the conventional art. Also, since there is no need to use a dedicated computing unit, the gate amount can be reduced and power consumption can be reduced.

Further, the periodic boundary condition can be fixed during the time when calculation is performed for j-particles in the same minute cell, there is no need to select the periodic boundary condition whenever a j-particle is changed, and the periodic boundary condition may be selected whenever the minute cell including the j-particle is changed. Therefore, since the calculation amount of the coordinate difference is reduced, the present invention provides still higher speed calculation.

The above and other objects, features, and advantages of the present invention will become apparent from the following description with reference to the accompanying drawings which illustrate examples of the present invention.

DESCRIPTION OF THE PREFERRED EMBODIMENTS

First, explanations are given of the operation principle of the coordinate difference calculation apparatus of the present invention. In the following, only the X coordinate is explained to simplify explanations.

Here, consideration is given to a case in which the force acting on a i-particle is calculated in accordance with the periodic boundary condition. In this case, the coordinate of an i-particle is set to (Xi, Yi, Zi), and the coordinate of $j_0$-particle (see, FIG. 1 to FIG. 3) existing in the same basic cell as i-particle is set to (Xj, Yj, Zj). Incidentally, since the $j_0$-particle indicates that all particles that are in the same basic cell as an i-particle, generally, there is a plurality of $j_0$-particles.

The distance between particles according to the periodic boundary condition is represented by the following equation 1.

$$\Delta Xj = (Xj - Xi) \pm Lx \qquad (Eq.1)$$

In equation 1, Lx is the length of one side of the basic cell in the X-axis direction. In this case, when attention is paid to an i-particle, the coordinate value of the i-particle is fixed during the time when the force acting on i-particle is calculated. Also, Lx is a fixed value. Then, above equation 1 is modified as follows in equation 2.

$$\Delta Xj = Xj - (Xi \mp Lx) \qquad (Eq.2)$$

In equation 2, the second term on the right side is the periodic boundary condition, and indicates any one of Xi, (Xi+Lx) and (Xi−Lx). The periodic boundary condition is a fixed value despite $j_0$-particle during the time when the force acting on i-particle is calculated. Therefore, the periodic boundary condition is calculated once and is stored in advance.

Also, as the periodic boundary condition, a value is selected among Xi, (Xi+Lx) and (Xi−Lx) so as to minimize the distance between the minute cell including an i-particle and the minute cell including a j-particle.

Figure 1:
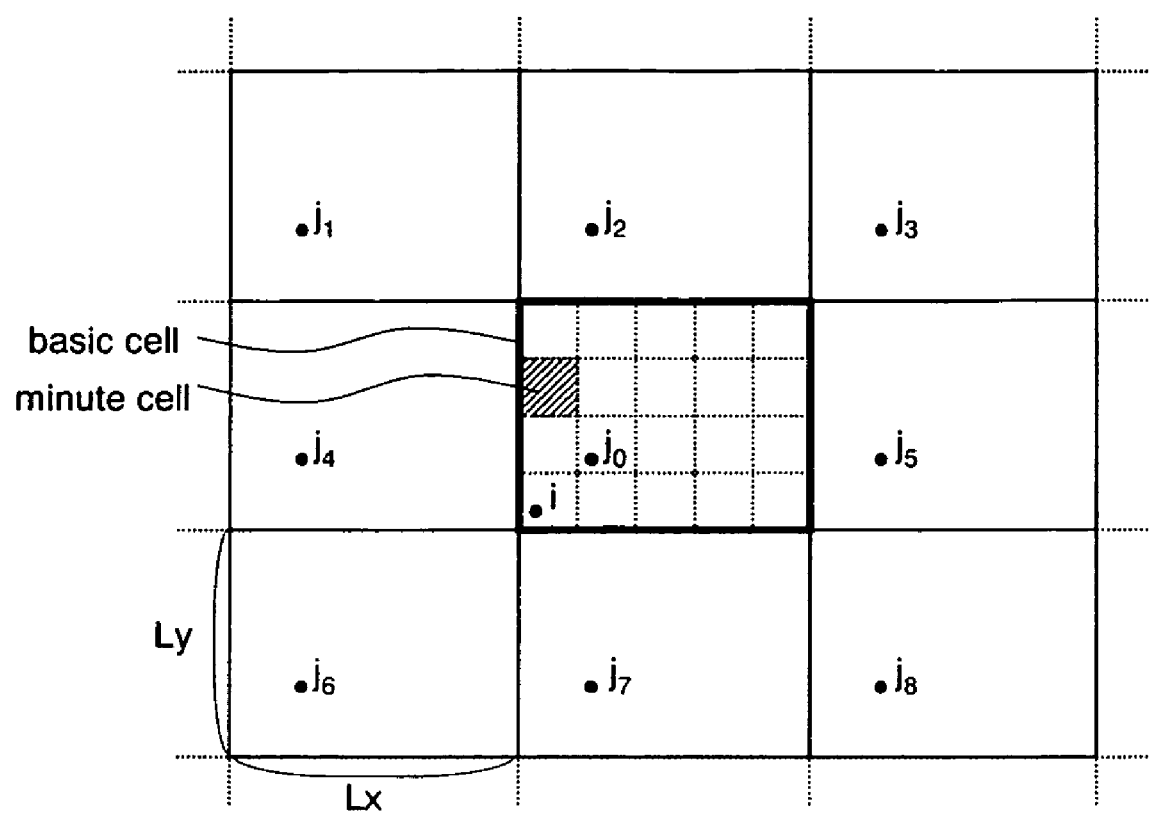
FIG. 1 is a two-dimensional view of an example showing basic cells in the XY plane.

Specifically, in the example in FIG. 1, among $j_0$- to $j_8$-particles, the $j_0$-particle that is in the same basic cell as the i-particle provides the minimum distance from the i-particle. When the $j_0$-particle is set as an object to be calculated, there is no need to add or subtract Lx to/from the coordinate of the $j_0$-particle. Therefore, Xi is selected as the periodic boundary condition. Similarly, when a calculation is performed while another particle in the same minute cell as the $j_0$-particle is regarded as a $j_0$-particle, the distance between the minute cell including the i-particle and the minute cell including the $j_0$-particle is minimized. Therefore, the periodic boundary condition is fixed to Xi, when calculation is performed for the $j_0$-particle in the same minute cell.

Figure 2:
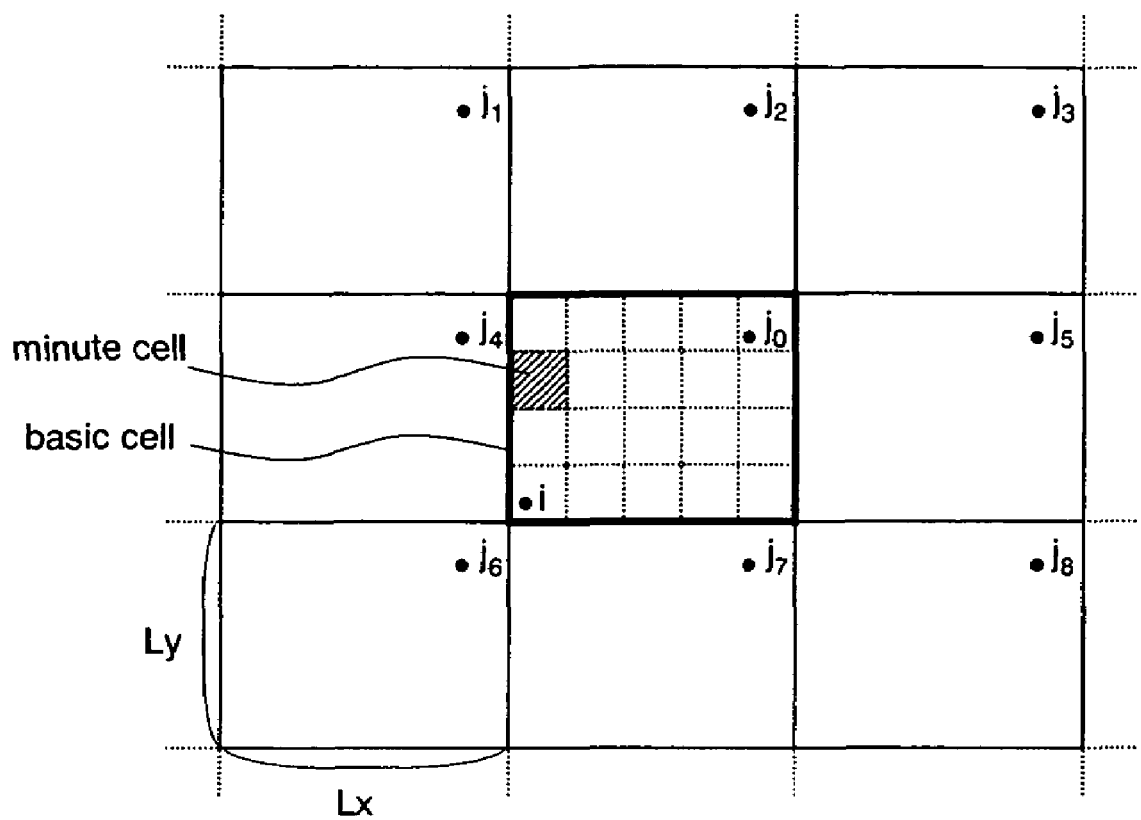
FIG. 2 is a two-dimensional view of another example showing basic cells in the XY plane.

Also, in the example in FIG. 2, among $j_0$- to $j_8$-particles, the minimum distance from the i-particle is provided by the $j_6$-particle in the surrounding basic cell, not by the $j_0$-particle in the same basic cell as i-particle. When the $j_6$-particle is set as an object to be calculated, there is a need to subtract Lx from the coordinate of the $j_0$-particle. Therefore, (Xi+Lx) is selected as the periodic boundary condition. Similarly, when calculation is performed while another particle in the same minute cell as the $j_0$-particle is regarded as a $j_0$-particle, the distance between the minute cell including the i-particle and the minute cell including the $j_6$-particle is minimized. Therefore, the periodic boundary condition is fixed to (Xi+Lx), when calculation is performed for the $j_0$-particle in the same minute cell.

Figure 3:
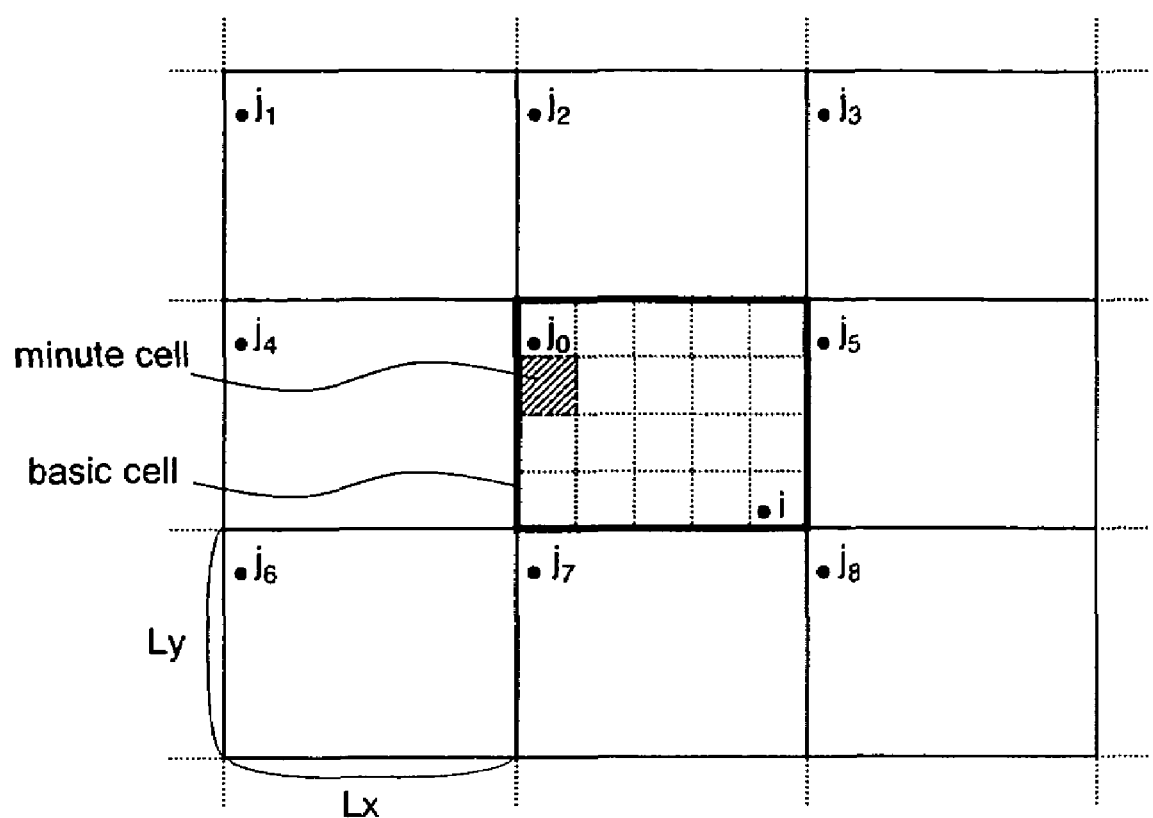
FIG. 3 is a two-dimensional view of further another example showing basic cells in the XY plane.

Also, in the example in FIG. 3, among $j_0$- to $j_8$-particles, the minimum distance from i-particle is provided by the $j_8$-particle in the surrounding basic cell, not by $j_0$-particle in the same basic cell as i-particle. When the $j_8$-particle is set as an object to be calculated, there is a need to add Lx to the coordinate of the $j_0$-particle. Therefore, (Xi−Lx) is selected as the periodic boundary condition. Similarly, when calculation is performed while another particle in the same minute cell as $j_0$-particle is regarded as a $j_0$-particle, the distance between the minute cell including the i-particle and the minute cell including the $j_8$-particle is minimized. Therefore, the periodic boundary condition is fixed to (Xi−Lx), when calculation is performed for the $j_0$-particle in the same minute cell.

As described above, the periodic boundary condition can be fixed when calculation is performed for j-particle in the same minute cell. Therefore, the periodic boundary condition that is calculated and stored in advance is changed whenever the minute cell including the i-particle is changed, thereby calculating the coordinate difference.

Therefore, according to the present invention, since there is no need to dynamically calculate the periodic boundary condition whenever a j-particle is changed, the coordinate difference can be calculated at high speed without using a dedicated computing unit.

Hereinafter, explanations are given of the configuration of the coordinate difference calculation apparatus that performs the operation with the above-mentioned principle according to an embodiment of the present invention.

Figure 4:
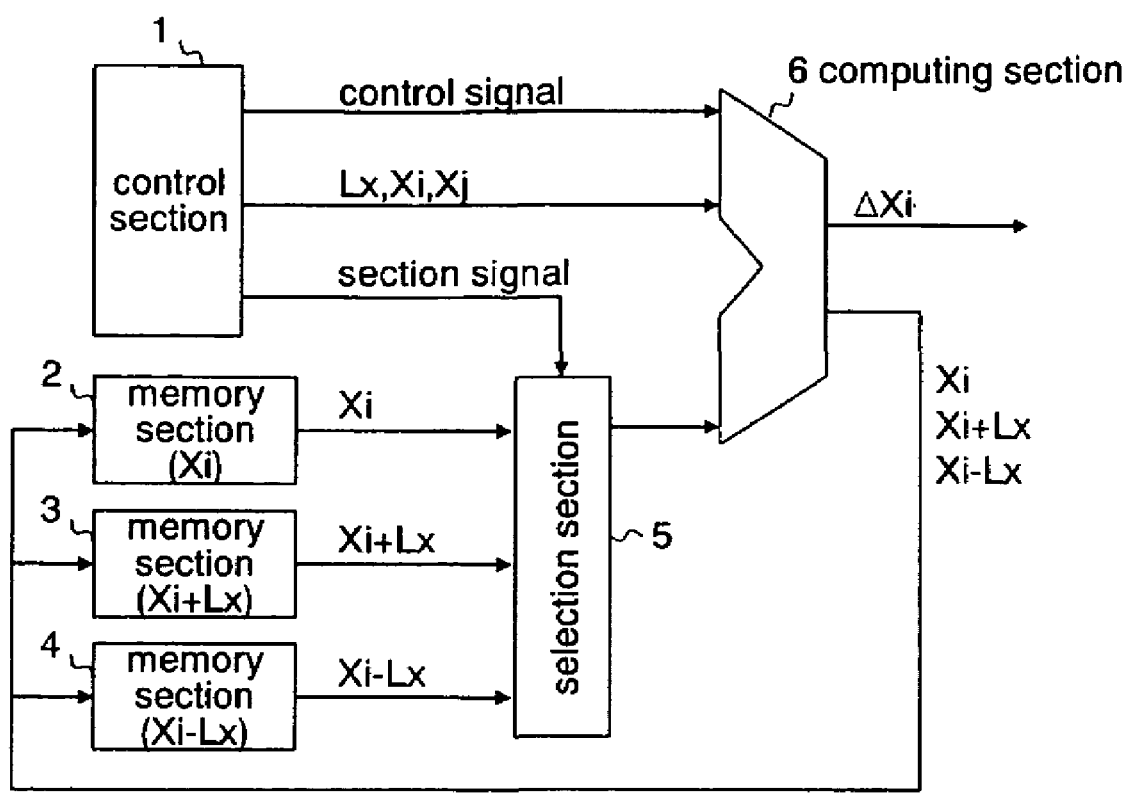
FIG. 4 is a block diagram showing a configuration of a coordinate difference calculation apparatus according to an embodiment of the present invention.

FIG. 4 is a block diagram showing the configuration of the coordinate difference calculation apparatus according to the present embodiment. Incidentally, the elements in FIG. 4 are provided for each of the X-coordinate, the Y-coordinate and the Z-coordinate, however, FIG. 4 shows only the elements for the X-coordinate, and elements for the Y-coordinate and the Z-axis are omitted.

Referring to FIG. 4, the coordinate difference calculation apparatus according to the present embodiment is provided with control section 1, memory sections 2 to 4, selection section 5, and computing section 6.

Control section 1 controls selection section 5 and computing section 6. Specifically, control section 1 outputs Lx that is the length of one side of the basic cell in the X-axis direction, Xi that is the X-coordinate value of the i-particle, and Xj that is the X-coordinate value of the j-particle, as parameters used for computing, and outputs a control signal for specifying the contents of operation of computing section 6. Also, control section 1 gives selection section 5 a section signal that is used to select a value among Xi, (Xi+Lx) and (Xi−Lx) in order to minimize the distance between the minute cell including i-particle and the minute cell including a j-particle.

Additionally, the coordinate difference calculation apparatus of the present embodiment is provided with a memory, not shown, for storing each coordinate of each particle that will become an i-particle or a j-particle, the length of one side of the basic cell, and the periodic boundary condition to be selected in order to minimize the distance between the minute cell including an i-particle and the minute cell including a j-particle. Control section 1 reads information stored in this memory, as needed, and outputs the information to selection section 5 and computing section 6.

Storage section 2 is a first storage section for storing in advance the value of Xi, storage section 3 is a second storage section for storing in advance the value of (Xi+Lx) obtained by adding Lx to Xi, and storage section 4 is a third storage section for storing in advance the value of (Xi−Lx) obtained by subtract Lx from Xi.

Selection section 5 selects and outputs one value from among Xi, (Xi+Lx) and (Xi−Lx) that are respectively stored in storage sections 2 to 4 in accordance with the selection signal output from control section 1.

Computing section 6 performs the operation in accordance with the control signal output from control section 1. Specifically, computing section 6 computes ΔXj by subtracting the output value of selection section 5 from Xj in accordance with Xj output from control section 1 and the value output from selection section 5, and computes (Xi+Lx) and (Xi−Lx) in accordance with Xi and Lx output from control section 1. Also, computing section 6 stores Xi output from control section 1 in storage section 2 and stores each (Xi+Lx) and (Xi−Lx) that are computed in storage sections 3, 4, respectively.

Hereinafter, explanations are given of the operation of the coordinate difference calculation apparatus shown in FIG. 4 with reference to FIG. 5 and FIG. 6.

Figure 5:
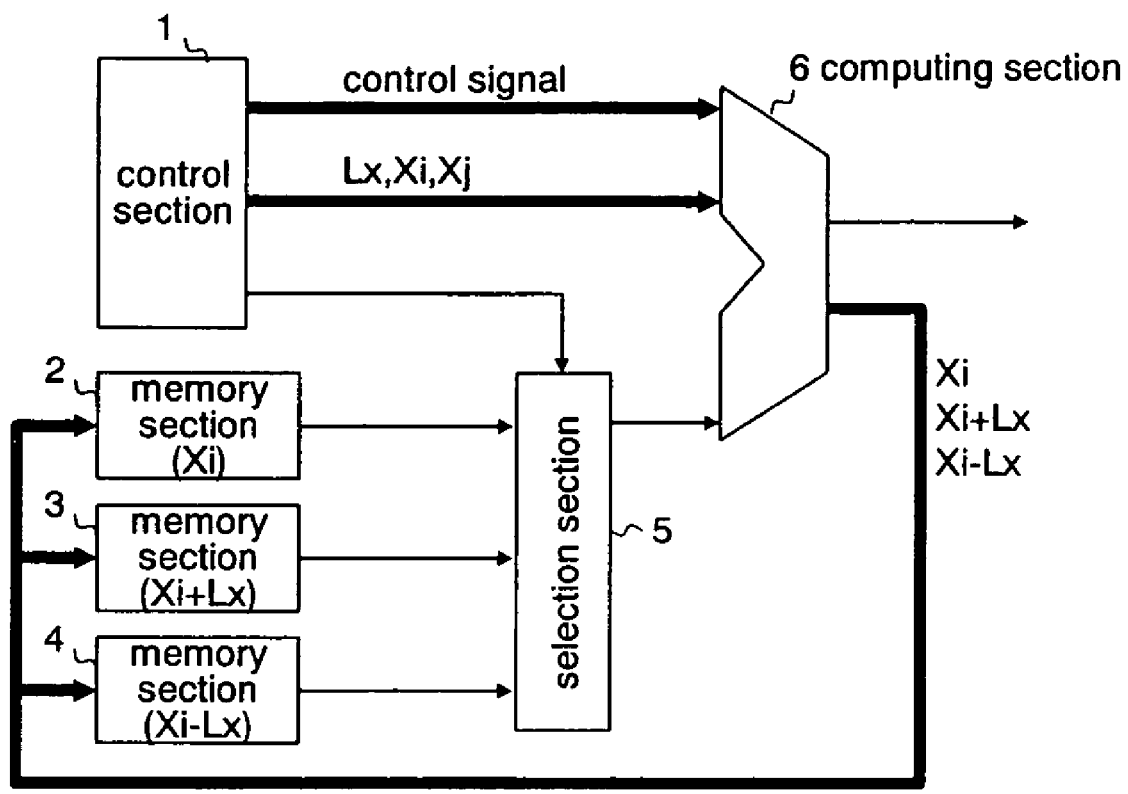
FIG. 5 is a diagram for explaining the operation of calculating and storing in advance the periodic boundary condition in the coordinate difference calculation apparatus shown in FIG. 4.

Referring to FIG. 5, first, control section 1 outputs Xi that is the X-coordinate of the i-particle and Lx that is the length of one side of the basic cell in the X-axis direction to computing section 6, and outputs the control signal to computing section 6 in order to perform the operation for storing Xi, (Xi+Lx) and (Xi−Lx) in storage sections 2 to 4, respectively.

In response to these, computing section 6 stores Xi output from control section 1 in storage section 2, as is, and computes (Xi+Lx) and (Xi−Lx) with Xi and Lx that are output from control section 1 and stores them in storage sections 3, 4.

Figure 6:
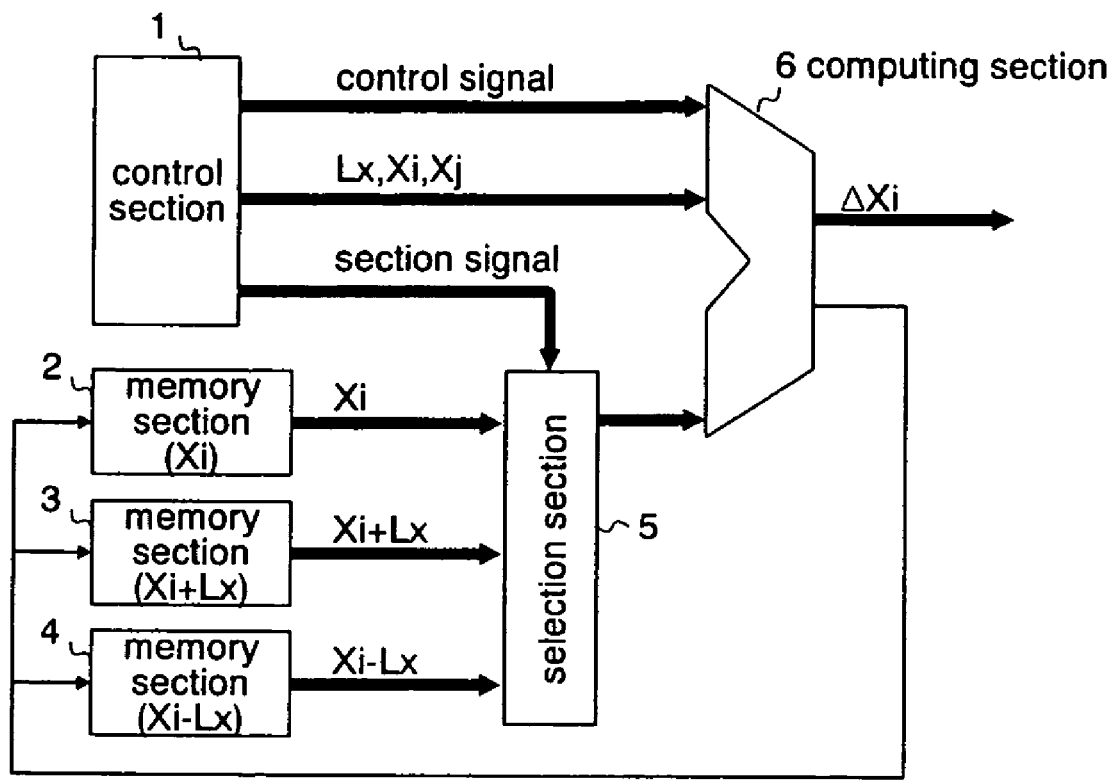
FIG. 6 is a diagram for explaining the operation of calculating a coordinate difference according to the periodic boundary condition that is stored in advance in the coordinate difference calculation apparatus shown in FIG. 4.

Referring to FIG. 6, successively, control section 1 selects one cell from among the minute cells in the same basic cell as an i-particle, further selects any particle from among the selected minute cell as $j_0$-particle, outputs Xj that is the X-coordinate of the selected $j_0$-particle to computing section 6, and outputs to computing section 6 the control signal that is used to perform the operation for subtracting the output value of selection section 5 from Xi.

Further, control section 1 outputs the selection signal to select a value that minimizes the distance between the minute cell including the i-particle and the minute cell including the j-particle among Xi, (Xi+Lx) and (Xi−Lx) stored in storage sections 2 to 4, respectively, to selection section 5.

Specifically, in the example in FIG. 1, the distance between the minute cell including the i-particle and the minute cell including the $j_0$-particle is minimum. Then, control section 1 outputs the selection signal for selecting Xi in order to regard the $j_0$-particle as the object to be calculated.

Also, in the example in FIG. 2, the distance between the minute cell including the i-particle and the minute cell including the $j_6$-particle is minimum. Then, control section 1 outputs the selection signal for selecting (Xi+Lx) in order to regard the $j_6$-particle as the object to be calculated.

Further, in the example in FIG. 3, the distance between the minute cell including the i-particle and the minute cell including the $j_8$-particle is minimum. Then, control section 1 outputs the selection signal for selecting (Xi−Lx) in order to regard the $j_8$-particle as the object to be calculated.

Successively, selection section 5 selects one value from among Xi, (Xi+Lx) and (Xi−Lx) stored in storage sections 2 to 4 in accordance with the selection signal output from control section 1 and outputs it to computing section 6. Then, computing section 6 computes ΔXj by subtracting the output of selection section 5 from Xj output from control section 1.

Subsequently, control section 1 sequentially outputs the X-coordinate of another $j_0$-particle in the same minute cell to computing section 6 while the selection signal is fixed, and terminates the calculation of ΔXj for all $j_0$-particles in the same minute cell. Then, when the calculation of ΔXj for all $j_0$-particles in the same minute cell is completed, control section 1 selects another minute cell in the basic cell, changes the selection signal in accordance with the selected minute cell, and calculates ΔXj for all $j_0$-particles in the minute cell, similarly to the above. However, there are cases in which the selection signal is not changed depending on the minute cell that is successively selected.

As described above, according to the present embodiment, the periodic boundary condition that is constant during the time when the force acting on i-particle is calculated, is calculated and stored in advance. Then, when the coordinate difference between the i-particle and the j-particle is calculated, the periodic boundary condition is selected to minimize the distance between the minute cell including the i-particle and the minute cell including the j-particle and the coordinate difference is calculated.

Therefore, since there is no need to dynamically calculate the periodic boundary condition whenever the j-particle is changed, the coordinate difference can be calculated at high speed without using a dedicated computing unit, which is different from the conventional art. Also, since there is no need to use a dedicated computing unit, the gate amount can be reduced and power consumption can be reduced.

Also, since the periodic boundary condition can be fixed when calculation is performed for j-particles in the same minute cell, there is no need to select the periodic boundary condition whenever a j-particle is changed, and the periodic boundary condition may be selected whenever the minute cell including the j-particle is changed. Therefore, since the calculation amount of the coordinate difference is reduced, it contributes to further speedup in the calculation.

While preferred embodiments of the present invention have been described using specific terms, such description is for illustrative purposes only, and it is to be understood that changes and variations may be made without departing from the spirit or scope of the following claims.

What is claimed is:

1. A coordinate difference calculation apparatus for calculating a coordinate difference between an i-particle and a j-particle included in one of a plurality of minute cells obtained by dividing a basic cell, comprising:
    a first storage section that stored in advance a coordinate value of said i-particle;
    a second storage section that stored in advance a value obtained by adding the length of one side of said basic cell to the coordinate of said i-particle;
    a third storage section that stored in advance a value obtained by subtracting the length of one side of said basic cell from the coordinate of said i-particle;
    a control section that outputs a selection signal to select a value in order to minimize a distance between a minute cell including said i-particle and a minute cell including said j-particle among values stored in said first to third storage sections and that outputs a coordinate value of said j-particle;
    a selection section that selects any one of the values stored in said first to third storage sections and outputs a selected value; and
    a computing section that subtracts the value output from said selection section from the coordinate value of said j-particle output from said control section.

2. The coordinate difference calculation apparatus according to claim 1, wherein said control section output in advance the coordinate value of said i-particle and the length of one side of said basic cell to said computing section, and
    wherein said computing section, in accordance with the coordinate value of said i-particle and the length of one side of said basic cell that are output from said control section, adds the length of one side of said basic cell to the coordinate of said i-particle, stores in advance said added value in said second storage section, subtracts the length of one side of said basic cell from the coordinate of said i-particle, stores in advance said subtracted value in said third storage section, and stores in advance said coordinate value of said i-particle output from said control section in said first storage section.

3. A coordinate difference calculation method of calculating a coordinate difference between an i-particle and a j-particle included in one of a plurality of minute cells obtained by dividing a basic cell, comprising:
    a first step of storing in advance a coordinate value of said i-particle in a first storage section;
    a second step of storing in advance a value obtained by adding the length of one side of said basic cell to the coordinate of said i-particle in a second storage section;
    a third step of storing in advance a value obtained by subtracting the length of one side of said basic cell from the coordinate of said i-particle in a third storage section;
    a fourth step of outputting a selection signal to select a value in order to minimize a distance between a minute cell including said i-particle and a minute cell including said j-particle among values stored in said first to third storage sections and of outputting a coordinate value of said j-particle;
    a fifth step of selecting any one of the values stored in said first to third storage sections and outputting a selected value; and
    a sixth step of subtracting the value that is output in said fifth step from the coordinate value of said j-particle that is output in said fourth step.

4. The coordinate difference calculation method according to claim 3, further comprising:
    a seventh step of outputting in advance the coordinate value of said i-particle and the length of one side of said basic cell:
    wherein in said first step, the coordinate value of said i-particle output in said seventh step is stored in advance in said first storage section;
    wherein in said second step, in accordance with the coordinate value of said i-particle and the length of one side of said basic cell that are output in said seventh step, the length of one side of said basic cell is added to the coordinate of said i-particle, and said added value is stored in advance in said second storage section; and wherein in said third step, in accordance with the coordinate value of said i-particle and the length of one side of said basic cell that are output in said seventh step, the length of one side of said basic cell is subtracted from the coordinate of said i-particle, and said subtracted value is stored in advance in said third storage section.

* * * * *

UNITED STATES PATENT AND TRADEMARK OFFICE
CERTIFICATE OF CORRECTION

| | | |
|---|---|---|
| PATENT NO. | : 7,468,510 B2 | Page 1 of 1 |
| APPLICATION NO. | : 11/585166 | |
| DATED | : December 23, 2008 | |
| INVENTOR(S) | : Kiyoshi Baba | |

It is certified that error appears in the above-identified patent and that said Letters Patent is hereby corrected as shown below:

Column 6, line 55, delete "Xi" and insert --Xj--.

Signed and Sealed this

Twenty-fifth Day of August, 2009

David J. Kappos
*Director of the United States Patent and Trademark Office*